(12) United States Patent
Nerandzic et al.

(10) Patent No.: US 11,678,951 B2
(45) Date of Patent: Jun. 20, 2023

(54) DETECTION OF RESIDUAL FLUID IN ENDOSCOPE CHANNELS

(71) Applicant: American Sterilizer Company, Mentor, OH (US)

(72) Inventors: Michelle M. Nerandzic, Lakewood, OH (US); Kathleen M. Antloga, Chardon, OH (US)

(73) Assignee: American Sterilizer Company, Mentor, OH (US)

( * ) Notice: Subject to any disclaimer, the term of this patent is extended or adjusted under 35 U.S.C. 154(b) by 386 days.

(21) Appl. No.: 17/060,847

(22) Filed: Oct. 1, 2020

(65) Prior Publication Data
US 2022/0104916 A1    Apr. 7, 2022

(51) Int. Cl.
*A61B 90/70* (2016.01)
*A61B 1/012* (2006.01)
*G01N 21/78* (2006.01)
*G01N 21/79* (2006.01)

(52) U.S. Cl.
CPC .............. *A61B 90/70* (2016.02); *A61B 1/012* (2013.01); *G01N 21/78* (2013.01); *G01N 21/79* (2013.01); *A61B 2090/701* (2016.02); *A61B 2090/702* (2016.02)

(58) Field of Classification Search
CPC ... A61B 90/70; A61B 1/012; A61B 2090/701; A61B 2090/702; A61B 1/00131; A61B 1/122; A61B 1/00057; G01N 21/78; G01N 21/79
See application file for complete search history.

(56) References Cited

U.S. PATENT DOCUMENTS

| | | | |
|---|---|---|---|
| 4,931,051 A | * | 6/1990 | Castello .................. A61F 13/42 604/361 |
| 5,179,024 A | * | 1/1993 | Dahms ................. G01N 31/222 436/42 |
| 6,043,096 A | | 3/2000 | Evtodienko et al. |
| 6,699,331 B1 | | 3/2004 | Kritzler |
| 10,471,189 B2 | | 11/2019 | O'Keefe et al. |
| 2008/0251102 A1 | | 10/2008 | Haack et al. |

(Continued)

FOREIGN PATENT DOCUMENTS

| | | |
|---|---|---|
| JP | H0889477 A | 4/1996 |
| JP | 3406081 B2 * | 5/2003 |
| WO | WO 2018/199189 A1 | 11/2018 |

OTHER PUBLICATIONS

Loeve et al., "Scopes Too Flexible . . . and Too Stiff," IEEE Pulse, 1(3), pp. 26-41, Nov. 2010.

(Continued)

*Primary Examiner* — Dennis White
(74) *Attorney, Agent, or Firm* — Kusner & Jaffe

(57) ABSTRACT

A device and method for testing for the presence of liquid in a cannula of a medical instrument is described. The device includes a flexible guide member having a first end, a second end and a length extending from the first end to the second end, an elongated member arranged within the flexible guide member, and an absorbent material attached to one of the elongated member. The flexible guide member is inserted into the cannula, the flexible guide member is manipulated to cause the absorbent material to move through the cannula. The absorbent material is analyzed for the presence of liquid.

31 Claims, 4 Drawing Sheets

(56) References Cited

U.S. PATENT DOCUMENTS

| | | | |
|---|---|---|---|
| 2010/0139018 A1* | 6/2010 | Maslanka | A61B 90/70 15/104.05 |
| 2011/0106019 A1* | 5/2011 | Bagwell | A61M 25/00 604/267 |
| 2014/0237748 A1* | 8/2014 | Sweeney | B08B 1/006 15/210.1 |
| 2014/0250614 A1* | 9/2014 | Pisacane | B08B 1/006 15/104.05 |
| 2016/0010139 A1 | 1/2016 | MaKay et al. | |

OTHER PUBLICATIONS

Salloum, "How to Achieve Clinically Dry Medical Device Lumens," Witt/Salloum/Price & Associates Consulting, Cenorin LLC, Apr. 2020.

International Search Report issued in corresponding International Patent Application No. PCT/US2021/049192 dated Dec. 23, 2021.

Written Opinion of the International Searching Authority issued in corresponding International Patent Application No. PCT/US2021/049192 dated Dec. 23, 2021.

Alfa, M., "Impact of wet storage and other factors on biofilm formation and contamination of patient-ready endoscopes: a narrative review," Gastrointestinal Endoscopy vol. 91, No. 2, pp. 236-247, 2020.

Instruction Manual from Healthmark Industries, Co., Instructions for Use: HydroCheck Moisture Detection Test, Jan. 23, 2020. <http://www.healthmark.info/CleaningVerification/HydroCheck/HydroCheck_IFU_2020-01-23.pdf>.

\* cited by examiner

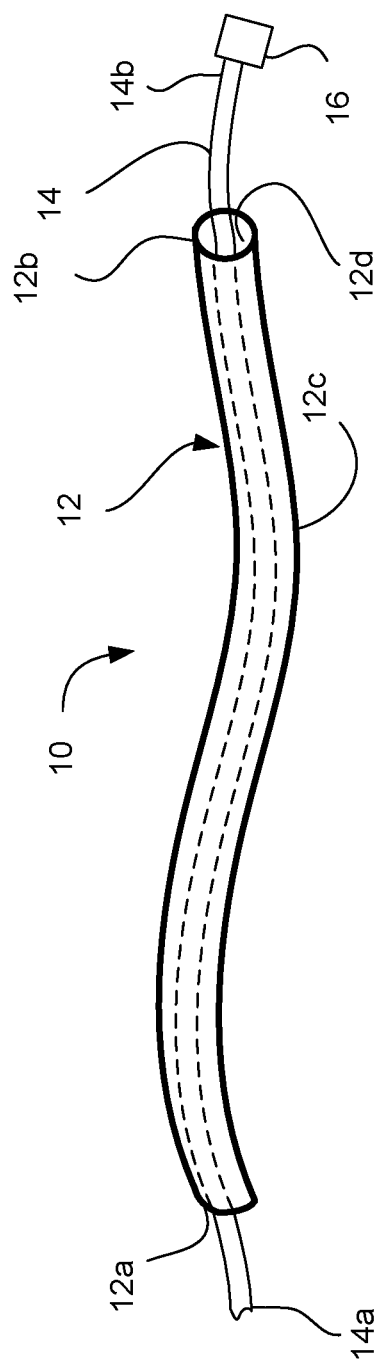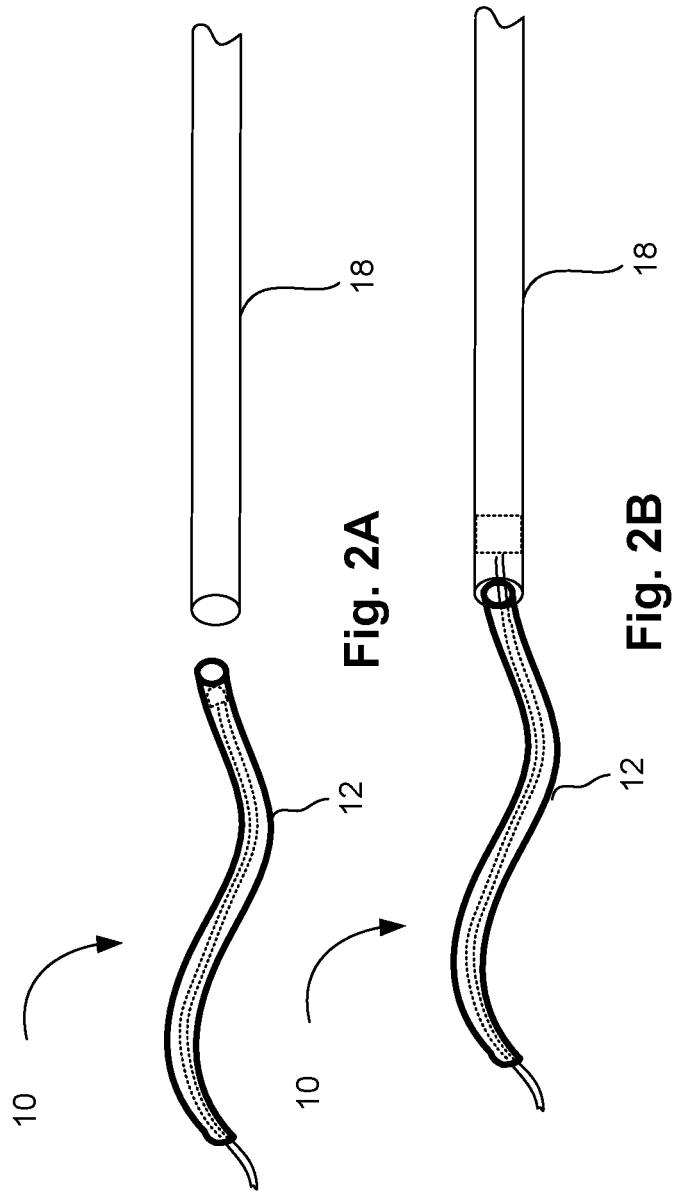

DETECTION OF RESIDUAL FLUID IN ENDOSCOPE CHANNELS

FIELD OF THE INVENTION

The present invention relates to an apparatus and method for detecting the presence of residual liquid in a channel of a medical instrument.

BACKGROUND OF THE INVENTION

Endoscopes and other elongated medical instruments are relatively expensive products. These instruments include one or more channels (also referred to as cannulas or lumens), through which surgical implements and other devices are passed during a surgical procedure. As used herein, a channel is defined as a tubular path or passage through which a fluid or gas may flow. During use, a channel may be exposed to bodily fluids and other materials that can accumulate on an inner surface of the channel. If the accumulated material is not thoroughly cleaned from the inner surface prior to disinfection and sterilization, surgical debris can be passed to another patient, leading to infection or other complications. It is thus critical to properly clean the interior surfaces of endoscopes and similar surgical instruments. However, these medical devices can include long, narrow, tortuous channels, which are often difficult to access and clean properly.

Another challenge includes properly determining if a channeled device is free of any residual liquid from a cleaning process. Channels of such devices are difficult or impossible to inspect visually. Standard protocols can be followed, but these do not always result in a properly dried device. Consequently, improved testing methods and novel devices are required to ensure that after cleaning a channeled medical instrument is properly dried.

One method in which a channel may be inspected for dryness is through a borescope. A borescope is an optical device made of either rigid or flexible tubing with an eyepiece or display on one end, and an objective lens or camera on the other linked together by an optical or electrical system in between. Some borescopes contain optics to provide light for enhanced imaging and to illuminate the object being examined. The image is magnified by the eyepiece or camera to aid in viewing. For examination of the internal channels of an endoscope, the borescope is typically inserted into the instrument channel opening at the distal tip of the endoscope. The borescope is slowly moved through the channel to visualize residual liquid or internal damage to the surface of the channel.

The borescope method has several limitations. First, the borescope is an effective method for examining large orifice channels that do not have sharp bends. However, many endoscopes are complex and contain very narrow-diameter channels. The borescope cannot be inserted into these narrow channels or curves with a small bend diameter. Second, a borescope is a relatively expensive piece of equipment, and departments that reprocess endoscopes do not often have this equipment. Third, not all borescopes can be easily disinfected or sterilized between uses. Therefore, there is a risk of cross contaminating an endoscope when the borescope is used on multiple endoscopes (since a borescope is not a single use device).

Another method for confirming dryness of the channels is through the use of water indicator paper. Water indicator paper utilizes test paper that is impregnated with either Copper Sulfate or Cobalt Chloride, which allows detection of water and water vapor. On contact with water the paper changes color, and the reaction is not reversible. For detection of residual liquid (water or alcohol) in the internal channels of an endoscope, compressed air is supplied to an opening on the endoscope and a piece of water indicator paper is used to catch/detect expelled liquid/moisture at the compressed air exit location.

Water indicator paper is an indirect method for detecting residual liquid in an endoscope. To use water indicator paper, compressed air is supplied to an opening on the endoscope and a piece of water indicator paper is used to catch/detect expelled liquid/moisture at the compressed air exit location. Studies have shown that up to 250 µL of liquid can be missed in some channels of an endoscope using this method. There are two main reasons that liquid can be missed. First, residual liquid can become resistant to moving by the compressed air if the air pressure, flow rate or flow principle is not optimal. Second, compressed air can evaporate residual liquid before it reaches the water indicator paper.

Yet another method for confirming dryness is through the use of a humidity logger. Humidity loggers use a sensor to collect data on relative humidity, dew point, and water vapor concentration from the atmosphere, in standard or metric units. For detection of residual liquid (water or alcohol) or humidity in the internal channels of an endoscope, compressed air is supplied to an opening on the endoscope and the humidity logger probe is placed at the air exit location.

The humidity logger also is an indirect method for detecting residual liquid in an endoscope. Similar to the water detection paper, compressed air is supplied to an opening on the endoscope and the humidity logger sensor is placed where air escapes to measure the humidity present in the air. A rigorous study to determine the limit of detection has not been performed for this method. However, one study has shown that the humidity logger can detect 5 µL of water. Detection of smaller quantities of residual liquid (water or alcohol) have not been determined.

There is currently no direct and sensitive method available for assessing endoscope channel dryness of all flexible endoscope internal channels.

SUMMARY OF THE INVENTION

A device and method in accordance with the invention detect residual liquid in endoscopes, but may be used to detect liquid in other sight occluded areas of medical devices. More specifically, a device is inserted into endoscope ports or directly into channels to detect residual liquids. The device, which contains a liquid absorbent material (water or alcohol), is of sufficient length to accommodate the entire length of the endoscope channels. In use, the device is inserted into the channel and then pulled out of the channel. The absorbent material then is analyzed to determine if liquid is present in the channel.

According to one aspect of the invention, a device for testing for the presence of liquid in a channel of a medical instrument includes: a flexible guide member having a first end, a second end and a length extending from the first end to the second end; an elongated member arranged within the flexible guide member; and an absorbent material arranged on at least one end of the elongated member.

In one embodiment, the absorbent material comprises a hydrophilic element.

In one embodiment, the absorbent material comprises a thread element having a first thread end and a second thread end, and at least one of the first thread end or the second thread end is frayed.

In one embodiment, only the first thread end is frayed.

In one embodiment, the second thread end is wound around the elongated member.

In one embodiment, the thread element is impregnated with a material that changes color in the presence of liquid.

In one embodiment, the thread element comprises at least one of a natural fiber or a synthetic fiber.

In one embodiment, the thread element comprises frayed cotton.

In one embodiment, the elongated member includes a thread element extending from both the first end and the second end of the guide member, and a stop is placed on a portion of the thread element extending from the second end, the stop preventing a portion of the thread element from entry into the second end of the guide member.

In one embodiment, the thread member comprises a first thread member and a second thread member different from the first thread member, the first thread member passes through the flexible guide member to extend from both the first end and the second end, and the second thread member is fixed to the first thread member.

In one embodiment, the second thread member is fixed to the first thread member by tying the second thread member to a portion of the first thread member extending from the second end.

In one embodiment, at least a portion of the thread element is twisted around the elongated member.

In one embodiment, the thread element is fixed to the elongated member using an adhesive.

In one embodiment, a rigidity of the elongated member is greater than a rigidity of the flexible guide member.

In one embodiment, the elongated member comprises a metallic wire.

In one embodiment, the guide member comprises a plastic tube.

In one embodiment, the plastic tube comprises PTFE.

According to another aspect of the invention, a method for testing for the presence of liquid in a channel of a medical instrument using a flexible guide member having a first end, a second end and a length extending from the first end to the second end, an elongated member arranged within the flexible guide member, and an absorbent material attached to one of the elongated member, includes: inserting the flexible guide member into the channel; manipulating the flexible guide member to cause the absorbent material to move through the channel; and analyzing the absorbent material for the presence of liquid.

In one embodiment, analyzing includes: placing the absorbent material in contact with a material that is sensitive to the presence of liquid; and viewing the response of the material to contact with the absorbent material.

In one embodiment, placing the absorbent material in contact with the material sensitive to the presence of liquid comprises placing the absorbent material in contact with at least one of copper sulfate indicator paper or cobalt chloride indicator paper.

In one embodiment, placing the absorbent material in contact with the material sensitive to the presence of liquid comprises placing the absorbent material in contact with copper sulfate solution or a cobalt chloride solution.

In one embodiment, placing the absorbent material in contact with the material sensitive to the presence of liquid comprises placing the absorbent material in contact with a Karl-Fischer solution, and transferring the Karl-Fischer solution to a Karl-Fischer titration or titrator.

In one embodiment, prior to inserting the flexible guide member into the cannula any remaining liquid in the cannula comprises a dye, and analyzing comprises viewing the absorbent material for the presence of the dye.

In one embodiment, the method includes using an absorbent material impregnated with a material that changes color in the presence of liquid, and analyzing comprises viewing the absorbent material for a change in color.

In one embodiment, the method includes using a thread element as the absorbent material, the thread element comprising a first thread end and a second thread end, and at least one of the first thread end or the second thread end is frayed.

In one embodiment, the second thread end is wound around the elongated member.

In one embodiment, the method includes using a thread element formed from at least one of a natural fiber or a synthetic fiber as the thread element.

In one embodiment, the method includes using a thread element formed from frayed cotton as the thread element.

In one embodiment, the method includes using an elongated member having a rigidity greater than a rigidity of the flexible guide member.

In one embodiment, using a metallic wire as the elongated member.

In one embodiment, the method includes using a plastic tube as the guide member.

According to another aspect of the invention, a device for testing for the presence of liquid in a channel of a medical instrument includes: a base configured to be grasped by a user; and at least one probe attached to the base, the at least one probe extending out from the base and comprising an absorbent material, wherein the at least one probe is configured to be inserted into a channel of a medical instrument.

In one embodiment, the base comprises a plurality of layers, and a portion of the at least one probe is arranged between the plurality of layers.

In one embodiment, the base comprises a planar surface.

In one embodiment, the base comprises at least one of a flexible material or an absorbent material.

To the accomplishment of the foregoing and related ends, the invention, then, comprises the features hereinafter fully described and particularly pointed out in the claims. The following description and the annexed drawings set forth, in detail, certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein:

FIG. 1 is a schematic diagram illustrating an exemplary device for detecting liquid in a medical instrument in accordance with the present invention.

FIG. 2A is a schematic illustration of the device of FIG. 1 just prior to insertion into a medical instrument.

FIG. 2B is a schematic illustration of the device of FIG. 1 after insertion into a medical instrument.

DETAILED DESCRIPTION OF PREFERRED EMBODIMENT

Figure 3:
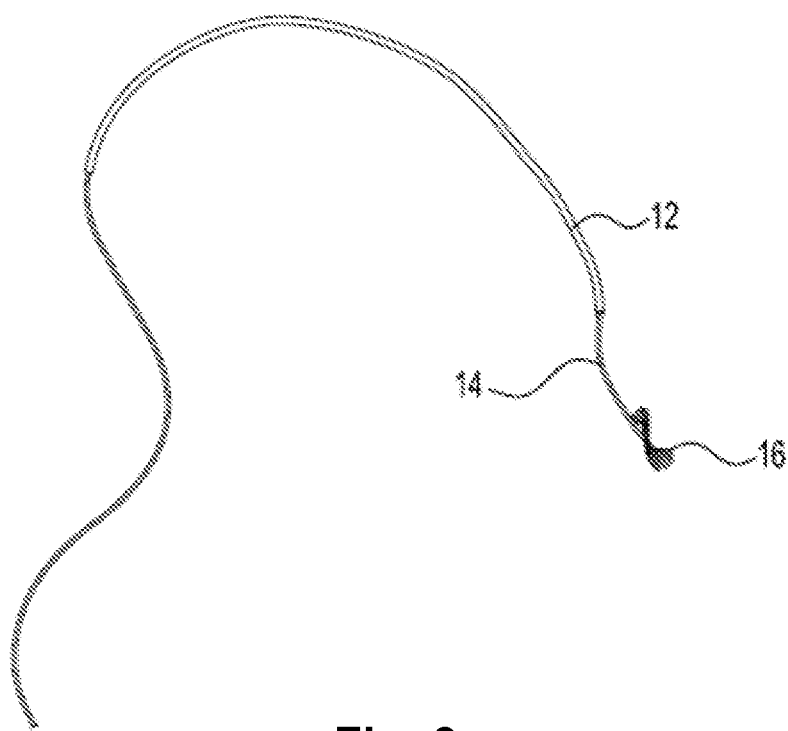
FIG. 3 illustrates an embodiment of the device of FIG. 1 wherein a thread is used as the absorbent material.

Embodiments of the present invention will now be described with reference to the drawings, wherein like reference numerals are used to refer to like elements throughout. It will be understood that the figures are not necessarily to scale.

In accordance with the present invention, a device is inserted into channels of an instrument, such as an endoscope, to detect residual liquids. The device is of sufficient length to accommodate the entire length of the channel, and contains an absorbent material to absorb liquid (water or alcohol) that may be in the channel. The device is inserted into the channel and then pulled out of the channel, and the absorbent material is analyzed for the presence of liquid.

In analyzing the absorbent material, a piece of copper sulfate indicator paper (e.g., sensitivity of 0.1 μL) may be placed in contact with the absorbent material. If moisture is present, the indicator paper will change color. Alternatively, the absorbent material may be inserted into a tube of copper sulfate solution (or other indicating chemical/dye solution) and colorimetric change is observed. In another variant, the absorbent material is impregnated with copper sulfate (or other indicating chemical/dye) and material changes from white to blue (or other color) when exposed to liquid inside the channel. Additionally, the liquid used to wet the channels may include a dye that is visually detectable on the absorbent material.

Referring now to FIG. 1, illustrated is an embodiment of a device 10 in accordance with the invention for testing for the presence of liquid in a channel of a medical instrument. The device 10 includes a flexible guide member 12 having a first end 12a, a second end 12b, and an enclosed structure 12c (e.g., a tube) extending between the two ends 12a, 12b. The guide member 12, while preferably circular in cross-section, may be formed in different shapes and have different diameters as required by the medical instrument to which the device will be used. For example, if the medical instrument has a circular channel having a 1 mm diameter, then the guide member 12 can be formed as a tube having a circular outer surface with a diameter less than 1 mm, e.g., 0.9 mm in diameter. The guide member 12 may be formed from a plastic material, such as polytetrafluoroethylene (PTFE), or other non-abrasive flexible material.

An elongated member 14 having a first end 14a and a second end 14b is arranged to slide within an inner channel 12d of the guide member 12. The elongated member 14 is of sufficient length so as to extend completely through the guide member 12 such that the first end 14a and the second end 14b extend out from the first end 12a and second end 12b, respectively, of the guide member 12. Preferably, the elongated member is dimensioned to fit within the channel, i.e., an outer dimension of the elongated member is smaller than an inner diameter of the channel. Arranged on the second end 14b of the elongated member 14 is an absorbent material 16, which collects residual liquid in the channel of the medical instrument. The absorbent material 16 may include or be formed as a hydrophilic element and/or may be impregnated with a material that changes color in the presence of liquid.

With additional reference to FIGS. 2A and 2B, illustrated is the device of FIG. 1 and an exemplary channel 18 of a medical device. In use, the absorbent material 16 may be pulled within the flexible guide 12, and the guide 12 inserted into the channel of the medical instrument 18. The flexible guide 12 is moved into the channel to an area of interest, and then the elongated member 14 is manipulated to push the absorbent material 16 out of the guide 12 to capture any liquid in the area of interest. Preferably, the absorbent material expands or otherwise conforms to the shape of the channel, thereby ensuring the entire region is swept by the absorbent material 16.

In one embodiment, the elongated member 14 is formed from a thread or thread-like material. In another embodiment, the elongated member 14 is formed from a metal wire, such as steel, aluminum or other metallic material. Preferably, a rigidity of the elongated member 14 is greater than a rigidity of the flexible guide member 12. By using an elongated member 14 that is more rigid than the guide member 12, the guide member 12 can be more easily worked through the channel of the medical instrument, protecting the channel from abrasion.

The absorbent material 16 may be formed from various materials. For example, in one embodiment the absorbent material is formed from a foam, sponge, or sponge-like material. Formation as a foam or sponge/sponge-like material is advantageous in that the absorbent material 16 can conform to the shape of the channel and ensure that contact is made with all inner surfaces as the device 10 is moved through the channel 18. In another embodiment, the absorbent material 16 is formed from natural (e.g., cotton) or synthetic fibers. For example, the absorbent material may be formed as a thread or thread-like element having a first thread end and a second thread end, where one or both of the first thread end and the second thread end is frayed. Fraying of one end increases the surface area of the absorbent material thus increasing the contact region of the absorbent material within the channel 18.

Figure 4:
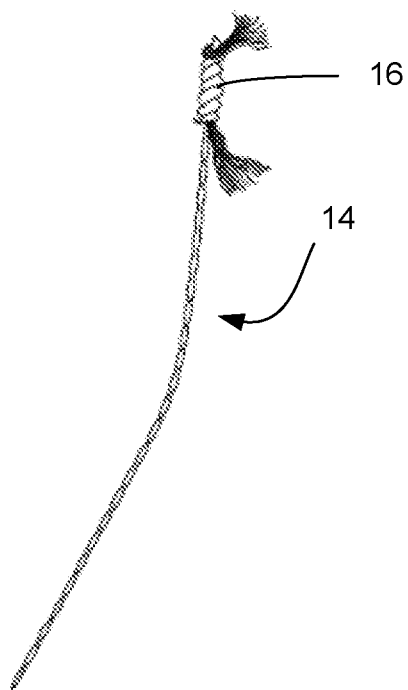
FIG. 4 illustrates absorbent material in the form of a thread attached to and wound around an elongated member in accordance with an embodiment of the invention.

The absorbent material 16 may be fixed to the elongated member 14 by an adhesive. For example, adhesive may be applied to the second end 14b of the elongated member 14 and/or on the foam or sponge material, and the two pieces are brought in contact with one another. FIG. 3 illustrates an embodiment in which the absorbent material 16, which is frayed on both ends, has a center portion bonded to the elongated member 14. Alternatively, a portion of the absorbent material 16 may be wound around the elongated member 14. For example, and with reference to FIG. 4, a portion of the absorbent material 16, which is in the form of a thread element, is twisted or tied around the elongated member 14. The other end or ends of the absorbent material 16 can extend away from the elongated member 14.

Figure 5:
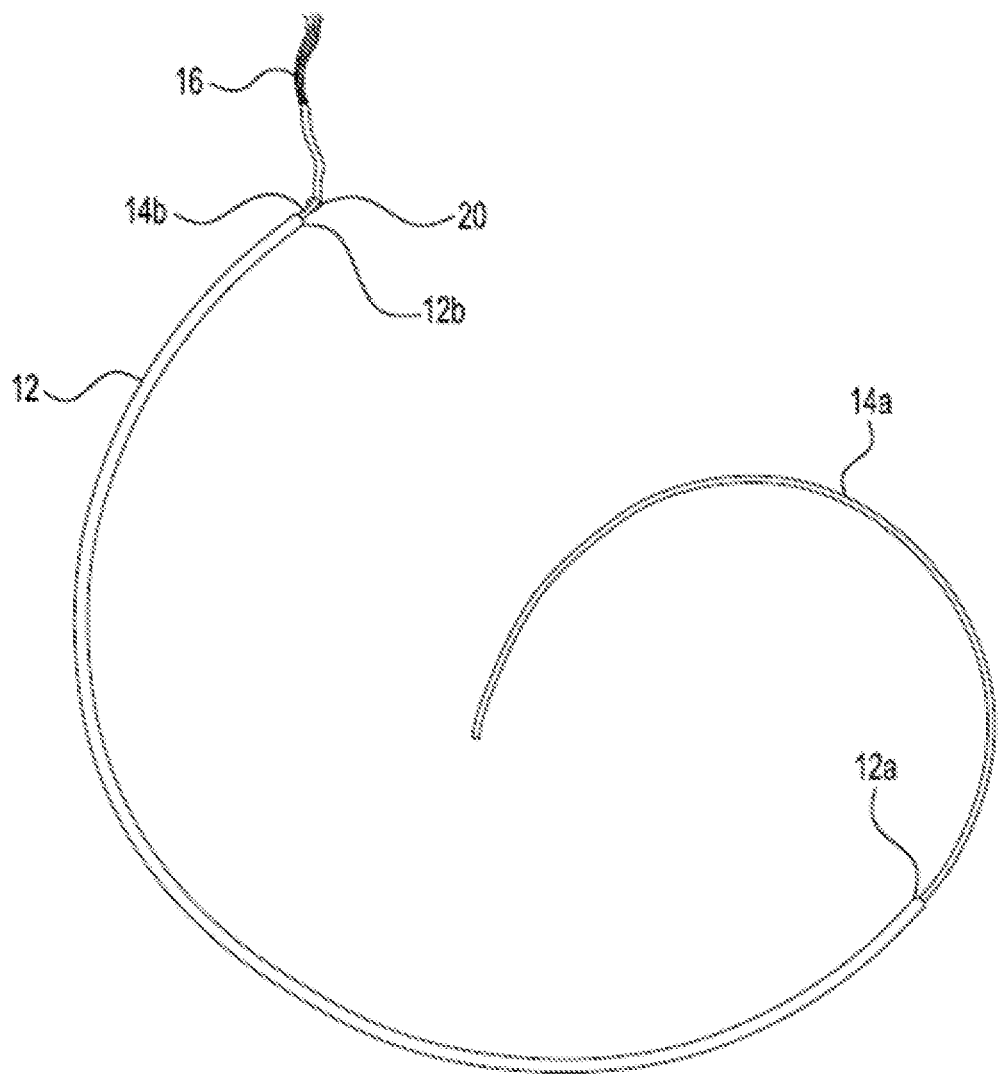
FIG. 5 illustrates absorbent material in the form of a thread attached to the elongated member in accordance in accordance with another embodiment of the invention.

In accordance with another embodiment, which is illustrated in FIG. 5, the elongated member 14 comprises a thread element extending from both the first end 14a and the second end 14b of the guide member 12. Preferably the thread element is formed with a material (or has material added thereto) that increases a rigidity of the thread such that it may be pushed through the guide member 12. A stop member 20 is placed on a portion of the elongated member 14 extending from the second end 12b. In the illustrated embodiment, the stop member 20 is formed by tying a knot in the thread element. Other stop members may be in the form of a tube portion fixed to the elongated member 14, the diameter of the tube portion being larger than a diameter of the guide member 12. The stop member prevents a portion of the thread element from entry into the second end 12b of the guide member 12. Alternatively, the elongated member 14 may be formed from two different thread portions. For example, a first thread member can pass through the flexible guide member 12 to extend from both the first end 12a and the second end 12b of the guide member 12. A second thread member can be fixed to the first thread member, the two thread members having different properties, e.g., different rigidity, different absorption rates, different materials, etc.

For the embodiments in which the elongated member is formed as a thread element or other elongated absorbent material, the elongated member 14 can also act to absorb liquid. Further, such configuration may wick moisture into the guide member 12 with capillary action aiding in drawing liquid into the elongated member 14.

Advantages of the device in accordance with the invention is that it can provide a direct measurement, is sensitive, and can be used to detect liquid in any and all endoscope channels or ports. Further, the application of compressed air to the instrument channel is not required because the device is placed directly into the channel to collect residual liquid and, unlike a borescope, it can fit into small diameter channels.

Figure 6:
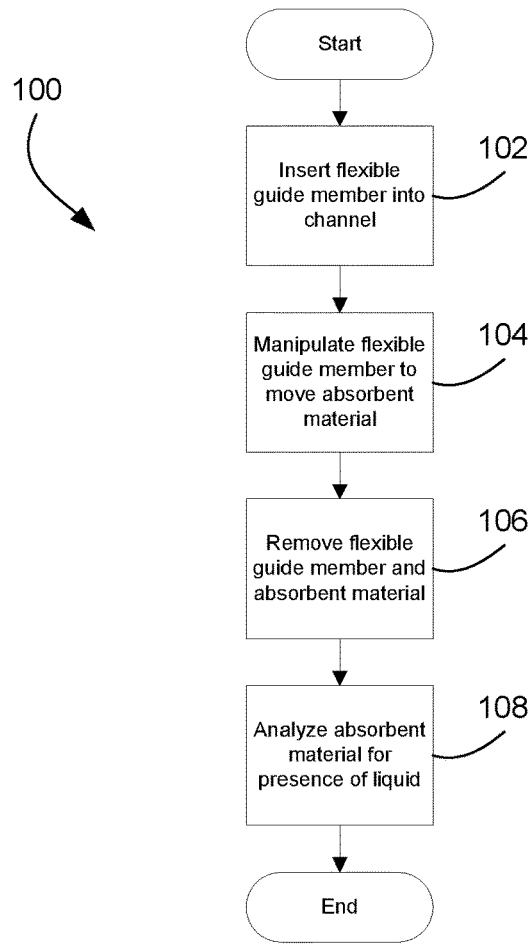
FIG. 6 is a flow chart illustrating exemplary steps of a method for detecting liquid in a medical instrument in accordance with the invention.

Moving now to FIG. 6, illustrated is a flow chart 100 that provides exemplary steps for testing for the presence of liquid in a channel of a medical instrument. The method is performed using a flexible guide member having a first end, a second end and a length extending from the first end to the second end, an elongated member arranged within the flexible guide member, and an absorbent material attached to one end of the elongated members. As should be appreciated, many alternatives and equivalents to the illustrated steps may exist and such alternatives and equivalents are intended to fall with the scope of the claims appended hereto. Alternatives may involve carrying out additional steps or actions not specifically recited and/or shown, carrying out steps or actions in a different order from that recited and/or shown, and/or omitting recited and/or shown steps. Alternatives also include carrying out steps or actions concurrently or with partial concurrence.

Beginning at step 102, the flexible guide member 12 is inserted into a channel of the medical instrument 18. In this regard, a flexible guide member 12 may be selected from a group of flexible guide members that has a diameter slightly smaller than a diameter of the channel. For example, if the channel has a diameter of 1 mm, then a guide member 12 have a diameter of 0.9 mm may be selected.

Next at step 104 the flexible guide member 12 is manipulated to cause the absorbent material 16 to move through the cannula. Such manipulation can include moving the elongated member 14 relative to the flexible guide member 12 (e.g., pushing, pulling and/or twisting the elongated member relative to the flexible member), thereby causing the end of the elongated member 14 (and thus the absorbent material 16) to move within the channel of the instrument 18. Further, the flexible guide member 12 itself may be moved relative to the instrument 18 to cause the elongated member 14 and absorbent material 16 to move within the channel. As a result, the absorbent material 16 traverses in the inner area of the channel and absorbs any liquid that may be within the channel.

After the flexible guide member 12 and/or elongated member 14 have been manipulated such that the absorbent material 16 has traversed an area of interest within the medical instrument 18, the flexible guide member 12, elongated member 14 and absorbent material 16 are withdrawn from the channel as indicated at step 106.

At step 108, the absorbent material 16 is analyzed for the presence of liquid. Such analysis can include placing the absorbent material 16 in contact with a material that is sensitive to the presence of liquid, and viewing the response of the material to contact with the absorbent material 16. For example, the absorbent material 16 may be placed in contact with copper sulfate indicator paper, cobalt chloride indicator paper, a copper sulfate solution or a cobalt chloride solution. After contact, the indicator paper or solution can be viewed for a change of color. Alternatively, placing the absorbent material 16 in contact with the material sensitive to the presence of liquid can include placing the absorbent material 16 in contact with a Karl-Fischer solution, and transferring the Karl-Fischer solution to a Karl-Fischer titrator or performing a Karl-Fischer titration. The solution then can be used to detect the presence of liquid by observing a change in color or the generation of electricity, for the Karl-Fischer titration or titrator, respectively.

Instead of placing the absorbent material 16 in contact with indicator paper or a solution, the absorbent material may be impregnated with a material that changes color in the presence of liquid and/or the liquid used to clean the medical instrument (and in particular the channel) may include a dye. The analyzing step then would simply involve viewing the absorbent material for a change in color. If the color changes, then liquid is present and if the color does not change, then liquid is not present.

Figure 7:
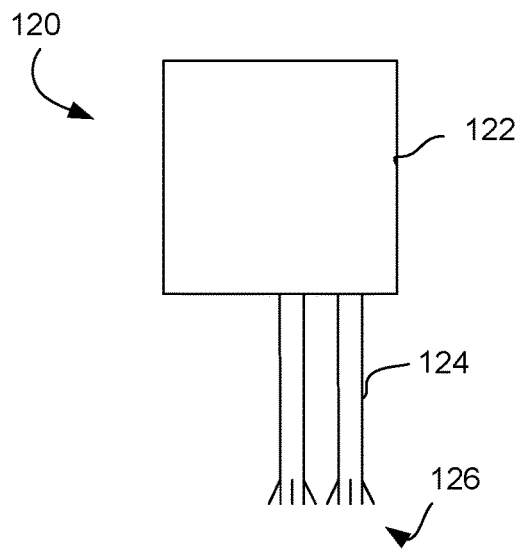
FIG. 7 is a schematic illustration of another device for detecting liquid in a medical instrument in accordance with the invention.

Referring now to FIG. 7, illustrated is another embodiment of a device for detecting liquid in a medical instrument in accordance with the invention. The device 120 includes a planar grip portion 122 (also referred to as a base) configured to be held between the thumb and one or more fingers of a user. In the illustrated embodiment the grip portion 122 has a square shape, although other shapes may be implemented provided they enable a user to hold the device 120. The grip portion 122 may be formed from a flexible material, such as plastic or like material. Alternatively, the grip portion 122 may be formed from a natural or synthetic material that can absorb liquid, and may be formed from multiple layers.

Extending out from the grip portion 122 is one or more absorbent probes 124. The probes 124 may be formed, for example, from an absorbent material such as natural or synthetic fiber, and are configured for insertion into a channel of a medical instrument under examination. The probes 124, which in the illustrated embodiment have frayed ends, absorb and wick away fluid in the channel. The frayed ends 126 increase the surface area of the probe 124, thereby ensuring that the probe contacts the inner surfaces of the channel. As will be appreciated, instead of frayed ends the tips of the probes 124 may be enlarged and/or formed from a compressible material, such as a synthetic or natural sponge material. To secure the probes 124 to the grip portion 122, at least a portion of the probes 124 may be arranged on or between layers of the grip portion 122. In this regard, an adhesive or other fastening means may be utilized to secure the probes 124 to the grip portion 122.

In use, a user grasps and manipulates the grip portion 122 to cause the probes 124 to contact and/or enter a channel of a medical instrument under investigation. The probes 124 sweep the inside of the channel and absorb any liquid that may be present. The user then manipulates the grip portion 122 to withdraw the probes 124 from the channel, and the probes 124 are analyzed for the presence of liquid. Such analysis may be the same as that described with respect to the other embodiments discussed herein.

Accordingly, a device and method in accordance with the invention can be used in any device that requires detection of residual liquid, such as endoscopes. However, the invention can be used to detect liquid in other sight occluded areas of medical devices that are required to be dry.

Although the invention has been shown and described with respect to a certain embodiment or embodiments, equivalent alterations and modifications may occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein exemplary embodiment or embodiments of the invention. In addition, while a particular feature of the invention may have been described above with respect to only one or more of several embodiments, such feature may be combined with one or more other features of the other embodiments, as may be desired and advantageous for any given or particular application.

What is claimed is:

1. A device for testing for the presence of liquid in a channel of a medical instrument, comprising:
   a flexible guide member having a first end, a second end and a length extending from the first end to the second end;
   an elongated member arranged within and movable through the flexible guide member; and
   an absorbent material arranged on at least one end of the elongated member.

2. The device according to claim 1, wherein the absorbent material comprises a hydrophilic element.

3. The device according to claim 1, wherein the absorbent material comprises a thread element having a first thread end and a second thread end, and at least one of the first thread end or the second thread end is frayed.

4. The device according to claim 3, wherein the thread element is impregnated with a material that changes color in the presence of liquid.

5. The device according to claim 3, wherein the thread element comprises at least one of a natural fiber or a synthetic fiber.

6. The device according to claim 3 wherein the thread element comprises frayed cotton.

7. The device according to claim 3, wherein the elongated member comprises a thread element extending from both the first end and the second end of the guide member, and a stop is placed on a portion of the thread element extending from the second end, the stop preventing a portion of the thread element from entry into the second end of the guide member.

8. The device according to claim 3, wherein the thread member comprises a first thread member and a second thread member different from the first thread member, the first thread member passes through the flexible guide member to extend from both the first end of the flexible guide member and the second end of the flexible guide member, and the second thread member is fixed to the first thread member.

9. The device according to claim 8, wherein the second thread member is fixed to the first thread member by tying the second thread member to a portion of the first thread member extending from the second end.

10. The device according to claim 3, wherein at least a portion of the thread element is twisted around the elongated member.

11. The device according to claim 3, wherein the thread element is fixed to the elongated member using an adhesive.

12. The device according to claim 3, wherein only the first thread end is frayed.

13. The device according to claim 12, wherein the second thread end is wound around the elongated member.

14. The device according to claim 1, wherein a rigidity of the elongated member is greater than a rigidity of the flexible guide member.

15. The device according to claim 14, wherein the elongated member comprises a metallic wire.

16. The device according to claim 1, wherein the guide member comprises a plastic tube.

17. The device according to claim 16, wherein the plastic tube comprises PTFE.

18. A method for testing for the presence of liquid in a channel of a medical instrument using a flexible guide member having a first end, a second end and a length extending from the first end to the second end, an elongated member arranged within the flexible guide member, and an absorbent material attached to one of the elongated member, the method comprising:
    inserting the flexible guide member into the channel;
    manipulating the elongated member to move through the flexible guide member to cause the absorbent material to move through the channel; and
    analyzing the absorbent material for the presence of liquid.

19. The method according to claim 18, wherein analyzing comprises:
    placing the absorbent material in contact with a material that is sensitive to the presence of liquid; and
    viewing the response of the material to contact with the absorbent material.

20. The method according to claim 19, wherein placing the absorbent material in contact with the material sensitive to the presence of liquid comprises placing the absorbent material in contact with at least one of copper sulfate indicator paper or cobalt chloride indicator paper.

21. The method according to claim 19, wherein placing the absorbent material in contact with the material sensitive to the presence of liquid comprises placing the absorbent material in contact with copper sulfate solution or a cobalt chloride solution.

22. The method according to claim 19, wherein placing the absorbent material in contact with the material sensitive to the presence of liquid comprises placing the absorbent material in contact with a Karl-Fischer solution, and transferring the Karl-Fischer solution to a Karl-Fischer titration or titrator.

23. The method according to claim 19, wherein prior to inserting the flexible guide member into the cannula any remaining liquid in the cannula comprises a dye, and analyzing comprises viewing the absorbent material for the presence of the dye.

24. The method according to claim 19, further comprising using an absorbent material impregnated with a material that changes color in the presence of liquid, and analyzing comprises viewing the absorbent material for a change in color.

25. The method according to claim 19, further comprising using a thread element as the absorbent material, the thread element comprising a first thread end and a second thread end, and at least one of the first thread end or the second thread end is frayed.

26. The method according to claim 25, wherein the second thread end is wound around the elongated member.

27. The method according to claim 25, further comprising using a thread element formed from at least one of a natural fiber or a synthetic fiber as the thread element.

28. The method according to claim 25, further comprising using a thread element formed from frayed cotton as the thread element.

29. The method according to claim 19, further comprising using an elongated member having a rigidity greater than a rigidity of the flexible guide member.

30. The method according to claim 29, further comprising using a metallic wire as the elongated member.

31. The method according to claim 18, further comprising using a plastic tube as the guide member.

* * * * *